(12) United States Patent
Gao (10) Patent No.: US 8,383,919 B2
(45) Date of Patent: Feb. 26, 2013

(54) HIGHLY FLUORESCENT PEPTIDE-METALLIC NANOCLUSTERS AS BIO-PROBES AND METHODS OF SYNTHESIS THEREOF

(76) Inventor: Xueyun Gao, Beijing (CN)

( * ) Notice: Subject to any disclaimer, the term of this patent is extended or adjusted under 35 U.S.C. 154(b) by 0 days.

(21) Appl. No.: 13/011,881

(22) Filed: Jan. 22, 2011

(65) Prior Publication Data

US 2011/0118441 A1    May 19, 2011

Related U.S. Application Data

(60) Provisional application No. 61/423,041, filed on Dec. 14, 2010.

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07K 1/00* | (2006.01) |

(52) U.S. Cl. ........ 977/773; 530/300; 530/345; 977/840; 977/920

(58) Field of Classification Search .................. None
See application file for complete search history.

(56) References Cited

U.S. PATENT DOCUMENTS

| | | |
|---|---|---|
| 2006/0099146 A1 | 5/2006 | Chow |
| 2009/0258355 A1 | 10/2009 | Maye |
| 2010/0009427 A1 | 1/2010 | Martinez |

OTHER PUBLICATIONS

Kong X-L et al. Biotechnology Letters 30(12):2071-2077, 2008.*
Tkachenko Ag, et al. J. Am. Chem. Soc. 125:4700-4701, 2003.*
Retnakumari A et al. Nanotechnology 21(5):2-12, 2010.*
Lin C-A J, et al. ACS Nano 3(2):395-401, Jan. 27, 2009.*
Wei H et al. Analyst 135(6):1406-1410, Jun. 2010.*
Jie Zhang, Fluorescent Noble Metal Nanoclusters, Ph.D. Thesis of Doctor of Philosophy in Chemistry, Georgia Institute of Technology, Apr. 2005.

\* cited by examiner

*Primary Examiner* — Robert Landsman
(74) *Attorney, Agent, or Firm* — Jie Tan (57) ABSTRACT

A method of one reaction step for synthesis of peptide template fluorescent metal nanoclusters as bioprobes. Specific targeting peptide containing a metal reactive group is synthesized and used to react with a metal salt solution under a sufficient pH condition at room temperature in forming peptide template fluorescent metal nanoclusters. The dialyzed metal nanoclusters is used directly as bio-probes.

16 Claims, 8 Drawing Sheets

HIGHLY FLUORESCENT PEPTIDE-METALLIC NANOCLUSTERS AS BIO-PROBES AND METHODS OF SYNTHESIS THEREOF

CROSS-REFERENCE

This application claims the priority of the U.S. Provisional Application No. 61/423041, filed on Dec. 14, 2010, the entirety of which is thereby incorporated by reference.

DESCRIPTION OF RELATED ART

The present application relates to metallic nanoclusers, and more particularly to a novel one-step method of synthesis of peptide bound metallic nanoclusters that can be used as biomolecule probes.

Note that the points discussed below may reflect the hindsight gained from the disclosed inventions, and are not necessarily admitted to be prior art.

Nanoclusters or nanoparticles of distinct electrical, optical and chemical properties have been synthesized and developed as biological and medical optical probes. Nanoclusters because of their small sizes (less than 10 nm) are more useful in intracellular probing and imaging than nanoparticles.

Organic dyes and fluorescent semi-conductor nanoparticles (e.g., quantum dots) ("QD") have been conventionally and commonly used for photo-sensing and imaging, and quantum dots within the size range of 3-5 nm have also been used as carriers to deliver molecules into cells. DNA and proteins can be coated or linked to the QD surface that has been multifunctionalized with a ligand. See, e.g., Patolsky, F., et al., *J. Am. Chem. Soc.* 125, page 13918 (2003). However, due to various drawbacks, such as poor photostability of the organic dyes, hush synthetic conditions and cytotoxicity of the semiconductor quantum dots, their applications in biological and medical imaging are limited.

Metallic nanoclusters have proved to be an advantageous alternative in that they can be made very small in size (<10 nm) and are stable and nontoxicity to cells. Metal nanoclusters have been immobilized with specific biomolecule to study functionality of organelle or intracellular biomolecular targets. For example, gold nanoclusters synthesized with mercaptoundecanoic acid (MUA) can be further modified with the nuclear localization signal peptide via 1-Ethyl-3-(3-dimethylaminopropyl) carbodiimide activation to mark nucleolus. See Lin, S. Y., et al., *Chemical Communication*, 39, pp 4762-4764 (2008).

Highly fluorescent gold nanoclusters for sub-cellular imaging have been synthesized using bovine serum albumin as a scaffold for the formation of gold nanoclusters by researchers, which has broad implications for biolabeling and disease diagnosis, was recently published in the *Journal of American Chemical Society*, 131, pp 888-889 (2009). The gold nanoclusters' nanometer sizes make it easy to target the nucleus inside the cell for sub-cellular biolabeling and bio-imaging. However, purified bovine serum albumin is expensive and the generated metal nanoclusters have to be further processed to conjugate with a bio-probe molecule before they are used as bio-probes.

US Patent Application US 2010/0029921 A1 provides a method of making functionalized gold nanoclusters by mixing prepared gold nanoclusters with thiolated DNA. The single stranded DNAs tagged with a fluorescent gold nanocluster may be used as DNA probe in various bioassays. However, this prepared gold nanoclusters may have a tendency toward self-agglomeration which broadens variations in nanocluster size range, and also fluorescence emission from non-DNA-attached nanoclusters can interfere with subsequent bioassays.

US Patent Application US 2010/0009427 A1 discloses a method of synthesis of fluorescent gold nanoclusters by mixing cysteine-rich peptide solution and chloroauric acid solution in a cold temperature and an acidic condition. However, the obtained nanoclusters have a broad emission of 640 nm with the supernatant of a maximum emission of 530 nm and the precipitate a maximum of 730 nm. The two emission wave lengths may result from two types of nanocluster structures. The inventor of this patent application never tested whether this final product was suitable for bio-probing. The mixture of non-uniform nanoclusters may not be suitable for targeted bio-imaging.

SUMMARY

The present application discloses a novel simple, easy to control, and consistent method for preparing highly fluorescent metal nanocluster bio-probes that can be directly used for bio-assays and bio-imaging and other photo-sensing technologies.

The synthesis of ready-to-use metal nanocluster bio-probes does not involve toxic chemicals or high temperatures. A single reaction of metal salt solution with a target-specific peptide terminated with one or more reducing amino acid produces scalable quantities of stable highly fluorescent metal nanoclusters conjugated with the peptide as bio-probe.

In one embodiment, the peptide is structured as X-Z, X being either at the N-terminal or the C-terminal portion of the peptide. Z includes a peptide sequence that is a functional motif for a specific bio-molecule, for example, a receptor, an antigen or signal sequence for organelles etc. X may include one or more amino acids selected from Arg, Asn, Asp, Cys, Gln, Glu, His, Trp, and/or Tyr.

In another embodiment, X represents a chemical group that contains at least one side group selected from hydroxybenzene, carboxylic, guanidino, amide, sulfhydryl, amidocyanogen, indole and/or imidazole.

In one embodiment, the reaction is conducted with the addition of alkaline solution at ambient temperature.

In one embodiment, the metal salt is silver nitrate.

In one embodiment, the metal salt is chloroauric acid.

In one embodiment, a re-suspended reaction from a dialysis or spin-cleaning is directly added to a cell culture for fluorescent bio-imaging or bio-assays.

This application provides a method and system for synthesis of metal nanoclusters based bio-probes in one easy reaction. The formed bio-probes are stable in aqueous solution as well as in the solid form, which facilitates their storage and distribution. Besides the low cost of the required reagents, the preparation is also environmentally friendly that does not involve toxic chemicals or high or low temperatures. In addition, the simple synthesis technique can be scaled up easily for mass production or scaled down to any customized small scale testing.

BRIEF DESCRIPTION OF THE DRAWINGS

The disclosed invention will be described with reference to the accompanying drawings, which show important sample embodiments of the invention and which are incorporated in the specification hereof by reference, wherein:

FIGS. 2A-2C show the fluorescent photo images of Hela cells with the bioprobe treatment of FIG. 1 as performed in Example 1 in accordance with this application. FIG. 2A shows a phase contrast image of the cells; FIG. 2B shows a fluorescent image of cells; FIG. 2C shows is a merged image of FIG. 2A and FIG. 2B.

FIGS. 4A-4C show the fluorescent photo images of Hela cells with the bioprobe treatment of FIG. 3 as performed in Example 2 in accordance with this application. FIG. 4A shows a phase contrast image of the cells; FIG. 4B shows a fluorescent image of cells; FIG. 4C shows is a merged image of FIG. 4A and FIG. 4B.

FIGS. 6A-6C show the fluorescent photo images of A549 cells with the bioprobe treatment of FIG. 5 as performed in Example 3 in accordance with this application. FIG. 6A shows a phase contrast image of the cells; FIG. 6B shows a fluorescent image of cells; FIG. 6C shows is a merged image of FIG. 6A and FIG. 6B.

FIGS. 8A-8C show the fluorescent photo images of 3T3 cells with the bioprobe treatment of FIG. 7 as performed in Example 4 in accordance with this application. FIG. 8A shows a phase contrast image of the cells; FIG. 8B shows a fluorescent image of cells; FIG. 8C shows is a merged image of FIG. 8A and FIG. 8B.

DETAILED DESCRIPTION OF SAMPLE EMBODIMENTS

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

Preparation of fluorescent metal nanoclusters involves using metal precursor solution (generally metal salt solution) and a template solution. As described in the US Patent Publication US 2010/0009427 A1, the types of template solutions includes poly(amidoamine) dendrimers, some polypeptides, and in some instance with the help of reducing agent. Although US 2010/0009427 A1 touches upon a method of using a cysteine rich polypeptide as template, it still suggests a two-step preparation for bio-probe attached metal nanoclusters, a nanocluster solution must be first prepared and then used as reaction base for further biomolecule attachment reaction.

However, researchers of metal nanoparticle structure have found that metal, such as gold, and sulfur atoms tend to aggregate in specific numbers and forming highly symmetrical geometries "superatoms" which can mimic the chemistry of single atoms of a completely different element. The X-ray structure study has revealed that pairs of organic sulfur ("thiolate") groups extracted gold atoms to form a linear thiolate-gold-thiolate bridge while interacting weakly with the metal surface of a metal core. These gold-thiolate complexes may form a protective crust around a metal atom core.

The inventor of this application reasoned that under proper molecule ratio, an exposed thio-group should directly induce the formation of metal nanocluster structure around and with the thiolate group. Therefore any thio-grouped peptide of specific targeting sequence is capable of inducing metal nanocluster formation by and with itself, forming a metal nanocluster bio-probe. Other metal reactive chemical groups may include hydroxybenzene, carboxylic, guanidino, amide, amidocyanogen, indole and imidazole.

Metallic nanoclusters templated with a peptide structure of X-Z were synthesized by mixing the solution of specific sequenced peptides and metallic salt at suitable pH, preferably at an alkaline pH to keep a thio-group thiolated. The X represents a reductive side chain or chemical group, such as hydroxybenzene, sulfhydryl, amidocyanogen and imidazole with function of reducing metal salt to form a metal cluster superstructure; X site may also be an amino acid selected a group including Arg, Asn, Asp, Cys, Gln, Glu, His, Trp and Tyr.

Z represents a peptide sequence having a specific sequence or structure that can function as a bio-probe for bioassays in vivo or in vitro. For example, Z may contain sequence of Cys-Cys-Tyr-Thr-Ala-Thr-$NH_2$ (SEQ ID NO: 1) for targeting the nucleus, X-Val-Val-Val-Cys-Cys-Cys-Arg-Lys-Val-Val-Cys-$NH_2$ (SEQ ID NO: 2) for targeting the nucleolus, Cys-Phe-Phe-Lys-Asp-Glu-Leu-$NH_2$ (SEQ ID NO: 3) for targeting endoplasmic reticulum, Gly-Ala-Ser-Asp-Tyr-Gln-Arg-Leu-Gly-Cys-$NH_2$ (SEQ ID NO: 4) for targeting trans-Golgi network, Cys-Lys-Gly-Gly-Ala-Cys-Leu-$NH_2$ (SEQ ID NO: 5) for targeting peroxisome, Lys-Phe-Glu-Arg-Gln (SEQ ID NO: 6) for targeting lysosome, Leu-Leu-Tyr-Arg-Ser-Ser-Cys-Leu-Thr-Arg-Thr-Ala-Pro-Lys-Phe-Phe-Arg-Ile-Ser-Gln-Arg-Leu-Ser-Leu-Met-$NH_2$ (SEQ ID NO: 7) for targeting mitochondrion, one structure of Phalloidin-cyclopeptide, $C_{35}H_{48}N_8O_{11}S$, or Ala-Val-Trp-Ala-Pro-Met-Thr-$NH_2$ (SEQ ID NO: 8) for binding actin, Asn-Leu-Arg-Ile-Ala-Leu-Arg-$NH_2$ (SEQ ID NO: 9) for binding microtubule, or Gly-Trp-Trp-Leu-Ala-Leu-Ala-Leu-Ala-P-Ala-Leu-Ala-Leu-Ala-Leu-Trp-Trp-Ala-$NH_2$ (SEQ ID NO: 10) for binding cell membrane protein and their derivative proteins.

Z may contain specific binding sequence, for example, Z may contain sequence of Arg-Lys-Cys-Cys-Tyr-Ser-Leu-$NH_2$ (SEQ ID NO: 11) for binding epidermal growth factor receptor, Arg-Gly-Asp and its analogues for binding integrin, Phe-Cys-Phe-Trp-Lys-Thr-Cys-Thr-$NH_2$ (SEQ ID NO: 12)

and its analogues for binding somatostatin receptor, Glu-Gln-Arg-Leu-Gly-Asn-Gln-Trp-Ala-Val-Gly-His-Leu-Met-NH$_2$ (SEQ ID NO: 13) for binding gastrin-releasing peptide receptor, Asp-Tyr(SO$_3$H)-Met-Gly-Trp-Met-Asp-Phe-NH$_2$ (SEQ ID NO: 14) for binding gastrin receptor and cholecystokinin-2, Ser-Tyr-Ser-Met-Glu-His-Phe-Arg-Trp-Gly-Lys-Pro-Val-NH$_2$ (SEQ ID NO: 15) for binding melanocortin-1 receptor, or His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 16) for binding glucagon-like peptide-1 receptor and their derivatives.

During the reaction, the X site or sites play the role of deoxidizing metallic salts and forming and stabilizing a metallic nanocluster structure. Optionally, other reducing agents may be introduced. For a synthesis reaction, the concentration of X-Z peptides may range from 1 nmol/L to 1 mol/L, and the concentration of metallic salt may range from 1 nmol/L to 1 mol/L. The molar ratio between an X-Z peptide and a metallic salt may range from 100:1 to 1:200.

The metallic salts are preferably all soluble salts of said metals, including but not limited to nitrate, nitrite, thiocyanate, chloride, sulfate, organic-metal compounds. The reaction temperature is preferably at ambient temperature, and the pH may be either acidic or alkaline, preferably all alkaline, adjusted with sodium hydroxide.

EXAMPLE 1

Preparation of silver (Ag) nanocluster templated by Cys-Tyr-Gly-Ala-Tyr-Gly-Trp-Ile-Asp-Phe-NH$_2$ (SEQ ID NO: 17), a heptagastrin ligand for heptagastrin receptor located in lysosomes. See G. Czerwinski, et al., *Proc. Natl. Acad. Sci. USA*. vol 95, pp. 11520-11525, 1998.

The Cys-Tyr-Gly-Ala-Tyr-Gly-Trp-Ile-Asp-Phe-NH$_2$ (SEQ ID NO: 17) peptide and silver nitrate were purchased from Sigma company. A 200 μL peptide water solution (0.2M) was first diluted with 160 μL MILLI-Q™ water. Then a 100 μL silver nitrate solution (0.75M) was added to the diluent peptide solution by drops, the mixture was stirred for 3 to 5 minutes. Then the pH value was adjusted by adding 100 μL sodium hydroxide solution (0.5M). After stirring for 5 minutes, the mixture was maintaining at ambient temperature for 3 hours at dark to form Ag nanocluster. The Ag nanocluster solution was then dialyzed against water for several hours to eliminate excessive unbound peptides. Optionally, the reaction solution may be filtered through a commercially available molecular weight cut resin spin column, and the Ag nanoclusters be suspended in water.

Figure 1:
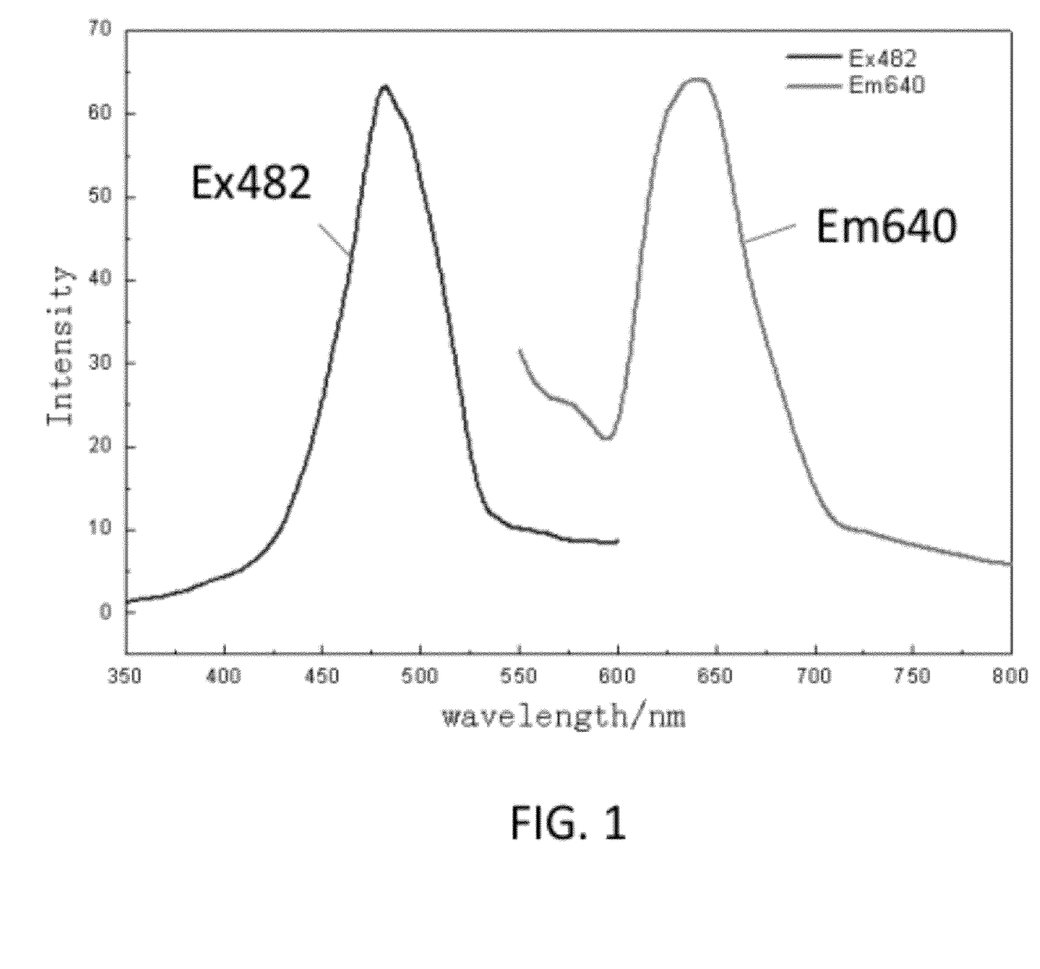
FIG. 1 shows an ultraviolet excitation and emission spectrometer of the Ag nanocluster templated with a peptide specific for lysosome organelle prepared in Example 1 in accordance with this application.

FIG. 1 shows the ultraviolet spectrometry of the excitation and the fluorescence emission of the Ag nanocluster solution obtained above. A narrow emission spectrum with maximum emission at 640 nm is seen with exciting wavelength ($\lambda_{ex}$) of 482 nm.

The above generated Ag nanocluster Ag solution was then co-incubated Hela cells to test its bio-probing specificity. Firstly proper amount of Hela cells were seeded into 96-well plates to reach a 60-70% confluency. After 24 hours' of cell culture, the Ag nanocluster solution supplemented with fetal bovine serum (FBS, 5% v/v) and penicillin-streptomycin (1% v/v) was added into the medium of the cell culture to the final concentration of 9 μM, the cells were then incubated for another 15 hours. The cells were then washed with ice-cold phosphate buffered saline (PBS, pH7.4) twice at 4° C., each time by shaking for 10 minutes. Covered with fresh PBS buffer, cells are visualized and photographed with confocal laser scanning microscopy (CLSM).

Figure 2:
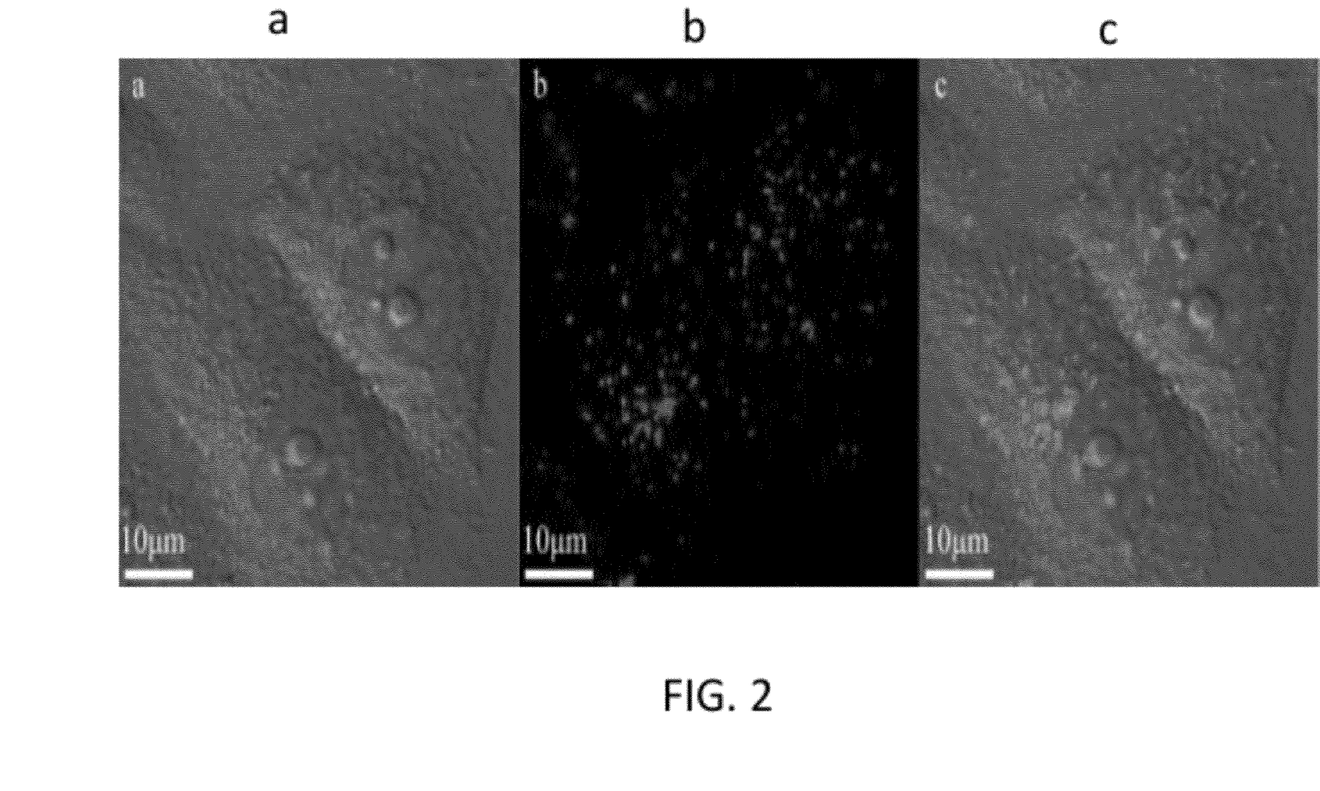

FIG. 2 shows the photos of cells under a confocal laser scanning microscope. Photo (a) is a phase contrast image of the cells; photo (b) is a fluorescent image of cells; photo (c) is a merged image of photo (a) and (b). The Ag nanoclusters specifically targeted the lysosomes, and the stained lysosome in Hela cell show a bright red emission, dispersed throughout the cell cytoplasm.

EXAMPLE 2

Preparation of Ag nanocluster templated by Arg-Lys-Cys-Cys-Tyr-Ser-Leu-NH$_2$, (SEQ ID NO: 18) a binding ligand sequence for epidermal growth factor receptor ErBb-2 which is located on the outside surface of cell membrane.

The Arg-Lys-Cys-Cys-Tyr-Ser-Leu-NH$_2$ (SEQ ID NO: 18) peptide and silver nitrate were purchased from Sigma company. Firstly 1000 μL peptides solution (0.2 M) was first diluted with 144 μL MILLI-Q™ water to form a diluent peptides solution. Then 16 μL silver nitrate solution (0.25M) was added to the peptide solution by drops, the mixture was stirred for 3 to 5 minutes. Then the pH value of the mixture was adjusted by adding 40 μL 0.5 M sodium hydroxide solution. After stirring for 5 minutes, the mixture was maintained at dark at ambient temperature for 18 hours to form Ag nanoclusters. The reaction mixture was then dialyzed against water for several hours to eliminate excessive unbound peptides. Optionally, the reaction solution may be filtered through a commercially available molecular weight cut resin spin column, and suspended in water.

Figure 3:
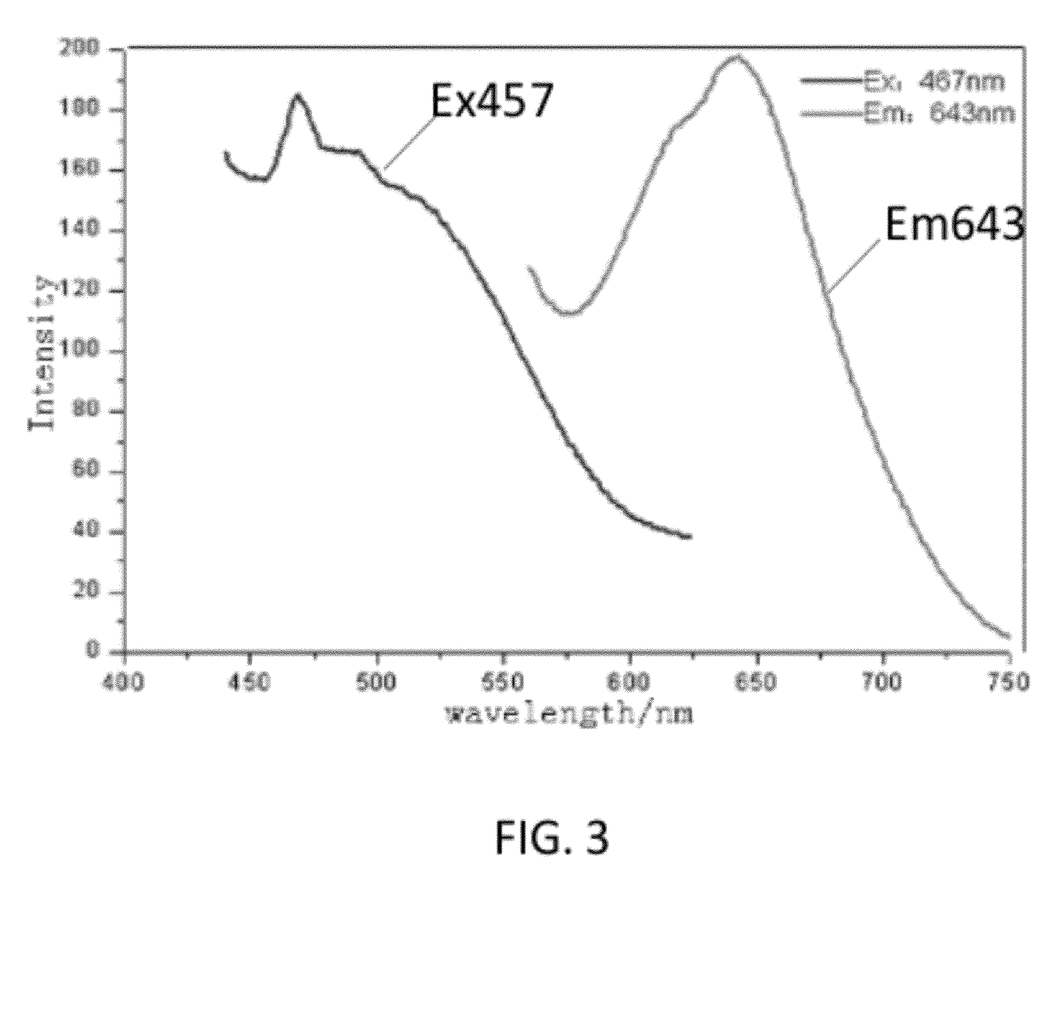
FIG. 3 shows an ultraviolet excitation and emission spectrometer of the Ag nanocluster templated with a peptide specific for epidermal growth factor receptor ErBb-2 prepared in Example 2 in accordance with this application.

FIG. 3 shows the ultraviolet spectrometry of the excitation and the fluorescence emission of the Ag nanocluster solution obtained in Example 2. A narrow emission spectrum with maximum emission at 643 nm is seen with exciting wavelength ($\lambda_{ex}$) of 467 nm.

The above generated Ag nanocluster solution was then co-incubated Hela cells to test its bio-probing specificity. Firstly Hela cells were seeded into 96-well plates at 60-70% confluency. After 24 hours' culture, the Ag nanocluster solution supplemented with fetal bovine serum (FBS, 5% v/v) and penicillin-streptomycin (1% v/v) was added into the cell culture to final concentration of 9.33 μM. After 15 hours of incubation, the cells were then washed with ice-cold phosphate buffered saline (PBS, pH7.4) twice at 4° C., each time shaking for 10 minutes. Covered with fresh PBS buffer, the cells are visualized and photographed with confocal laser scanning microscopy (CLSM).

Figure 4:
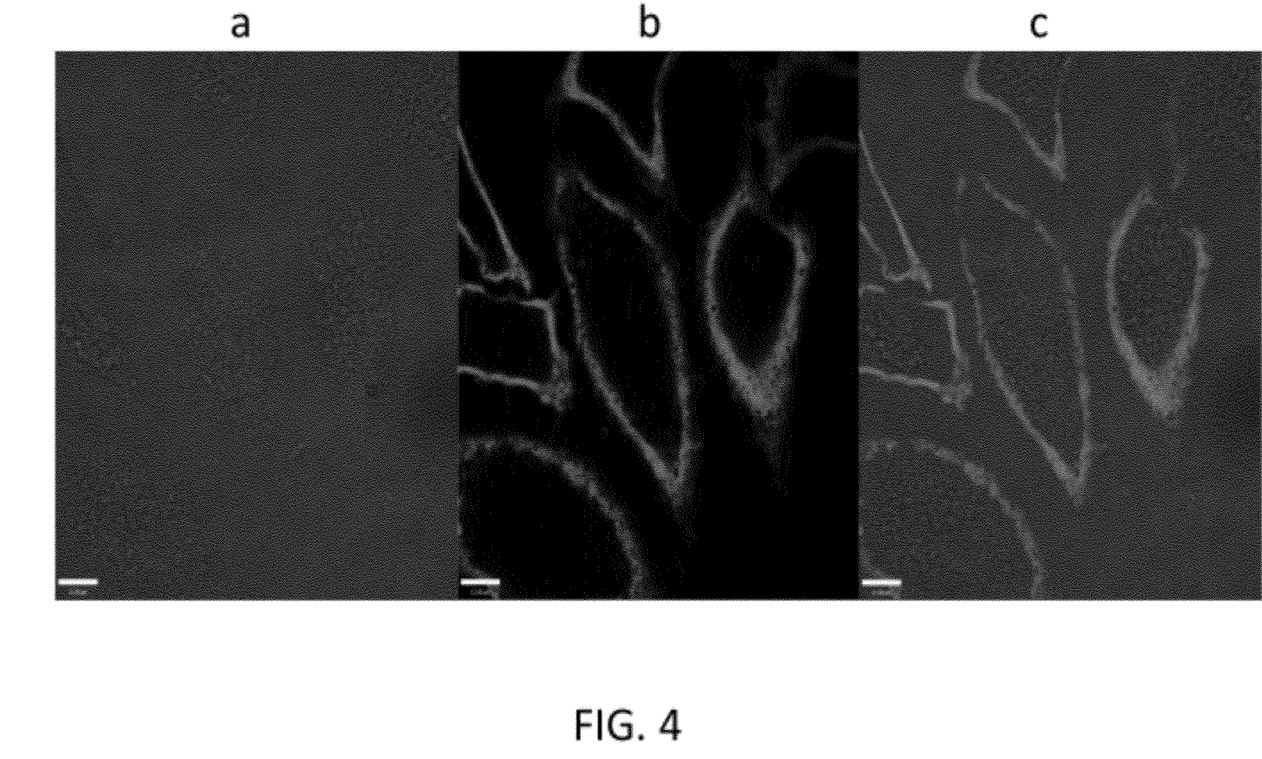

FIG. 4 shows the photos of cells under a confocal laser scanning microscope. Photo (a) is a phase contrast image of the cells; photo (b) is a fluorescent image of cells; photo (c) is a merged image of photo (a) and (b). The Ag nanoclusters specifically bound to the outside of cell membrane, and the stained Hela cell membranes show a bright red emission.

EXAMPLE 3

Preparation of gold (Au) nanocluster templated by Tyr-Gly-Arg-Lys-Lys-Arg-Arg-Gln-Arg-Arg-Arg-NH$_2$ (SEQ ID NO: 19), a nucleus location signal peptide from HIV-1 Tat Protein for nucleus targeting. See A. G. Tkachenko, et al., *Bioconjugate Chem.*, vol. 15, No. 3, pp 482-490, 2004.

The Tyr-Gly-Arg-Lys-Lys-Arg-Arg-Gln-Arg-Arg-Arg-NH$_2$ (SEQ ID NO: 19) peptide and chloroauric acid were purchased from Sigma company. Then 50 μL peptide solution (0.2 M) was added diluted with 144 μL MILLI-Q™ water to form a diluted solution. Secondly 16 μL chloroauric acid solution (0.75M) was added to the diluted peptide solution by drops, the mixture was then mixed by stirring for 3 to 5 minutes. The pH value of the reaction was adjusted by adding 40 µL sodium hydroxide solution (0.5M) and mixed by stirring for 5 minutes. The mixture was maintained at ambient temperature for over 24 hours at dark to form Au nanoclusters. The final reaction was then dialyzed against water for several hours to eliminate excessive unbound peptides. Optionally, the reaction solution may be filtered through a commercially available molecular weight cut resin spin column.

Figure 5:
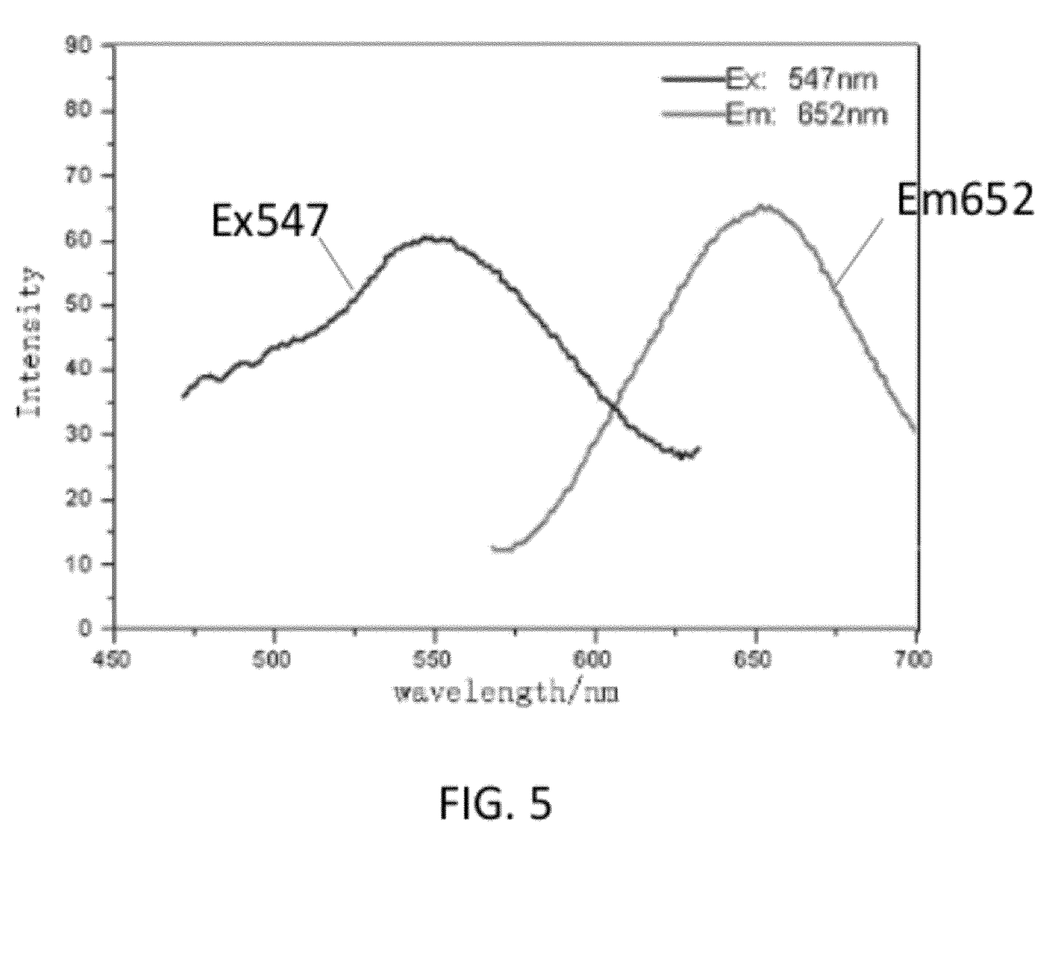
FIG. 5 shows an ultraviolet excitation and emission spectrometer of the Au nanocluster templated with a peptide specific for the nucleus prepared in Example 3 in accordance with this application.

FIG. 5 shows the ultraviolet spectrometry of the excitation and the fluorescence emission of the Au nanocluster solution obtained in Example 3. A narrow emission spectrum with maximum emission at 652 nm is seen with the exciting wavelength ($\lambda_{ex}$) of 547 nm.

The above generated Au nanocluster solution was then co-incubated A549 cells to test its bio-probing specificity. Firstly A549 cells were seeded into 96-well plates at 60-70% confluency. After 24 hours' culture, the Au nanocluster solution containing fetal bovine serum (FBS, 5% v/v) and penicillin-streptomycin (1% v/v) was added into the cell culture to final concentration of 9 µM for 15 hours. The cells then were washed with ice-cold PBS twice at 4° C. by shaking for 10 minutes each time. Covered with fresh PBS buffer, the cells are visualized and photographed with confocal laser scanning microscopy (CLSM)

Figure 6:
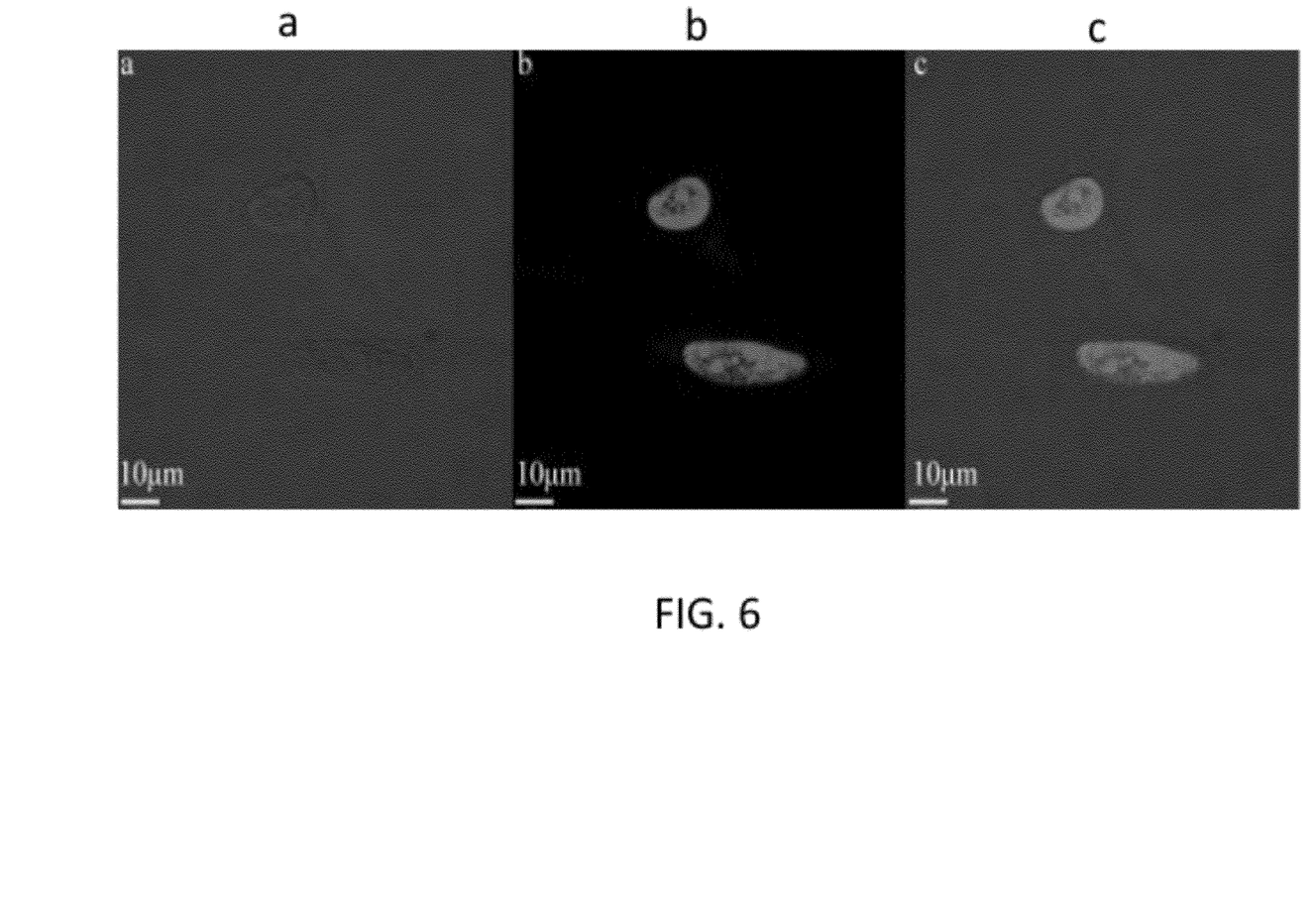

FIG. 6 shows the photos of Au nanocluster treated A549 cells under a confocal laser scanning microscope. Photo (a) is a phase contrast image of the cells; photo (b) is a fluorescent image of cells; photo (c) is a merged image of photo (a) and (b). The Au nanocluster probes were specifically located to the nucleus of the A549 cells, and the stained A549 nucleuses show a bright red emission.

EXAMPLE 4

Preparation of gold (Au) nanoclusters templated by Tyr-Arg-Phe-Lys-NH$_2$ (SEQ ID NO: 20) a specific sequence that binds cardiolipin protein located on the inner mitochondrial membrane in 3T3 cell. See K. Zhao et, al. *J. Biological Chem*, Vol. 279, No. 33, pp. 34682-34690, 2004.

The Tyr-Arg-Phe-Lys-NH$_2$ (SEQ ID NO: 20) peptide and chloroauric acid were purchased from Sigma Company. Firstly 400 µL of the peptide solution (0.4M) was diluted with 160 µL MILLI-Q™ water to form a diluted peptide solution. Secondly 16 µL chloroauric acid solution (0.6 M) was then added to the diluted peptide solution by drops, and the mixture was stirred for 3 to 5 minutes. Thirdly the pH of the reaction was then adjusted by adding 24 µL sodium hydroxide solution (0.5M). After stirring for 5 minutes, the mixture was maintained at ambient temperature for over 24 hours at dark to form Au nanoclusters. The final reaction was then dialyzed against water for several hours to eliminate excessive unbound peptides. Optionally, the reaction solution may be filtered through a commercially available molecular weight cut resin spin column.

Figure 7:
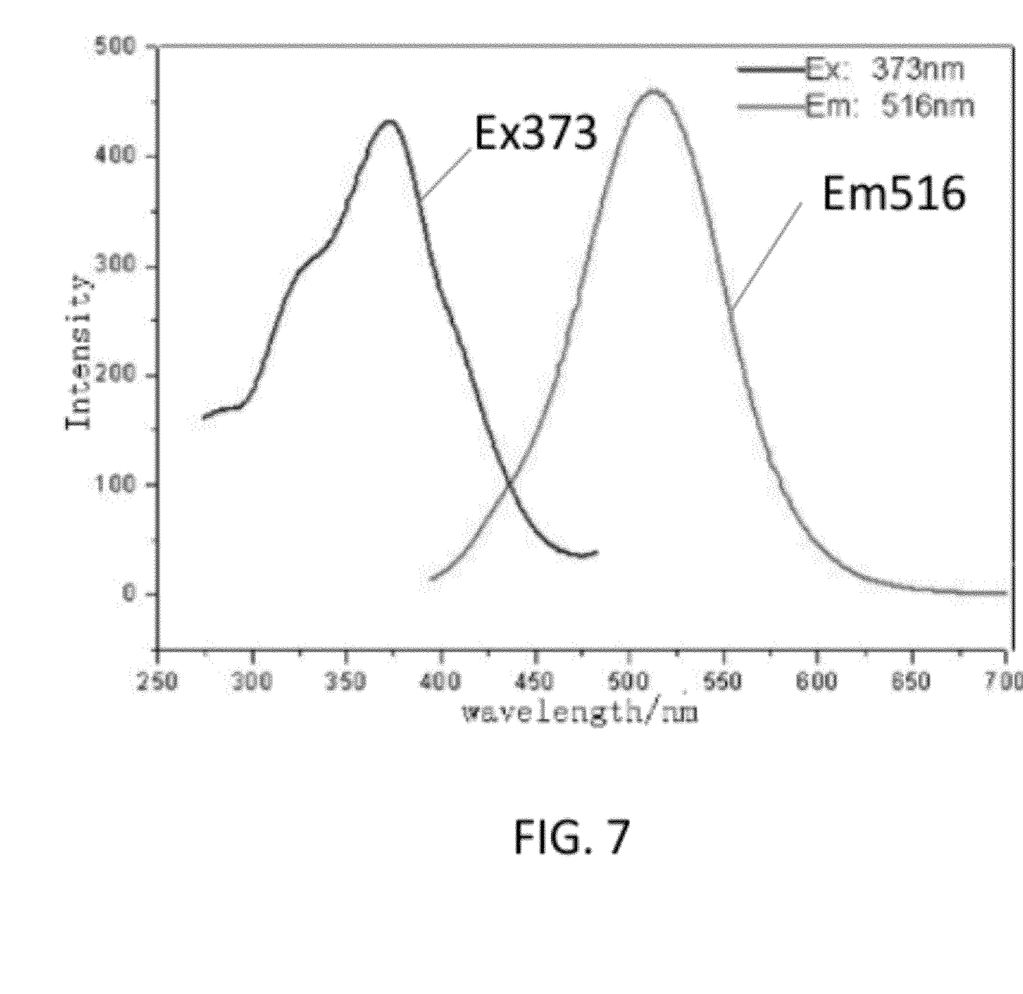
FIG. 7 shows an ultraviolet excitation and emission spectrometer of the Au nanocluster templated with a peptide specific for the mitochondrial inner membrane prepared in Example 4 in accordance with this application.

FIG. 7 shows the ultraviolet spectrometry of the excitation and the fluorescence emission of the Au nanocluster solution obtained in Example 4. A narrow emission spectrum with maximum emission at 516 nm is seen with the exciting wavelength ($\lambda_{ex}$) of 373 nm.

The above generated Au nanocluster solution was then co-incubated 3T3 cells to test its bio-probing specificity. Firstly 3T3 cells were seeded into 96-well plates at 60-70% confluence. After 24 hours' culture, the Au nanocluster solution containing fetal bovine serum (FBS, 5% v/v) and penicillin-streptomycin (1% v/v) was added into medium to a final concentration of 11 µM. After 15 hours incubation, the treated 3T3 cells were washed with PBS twice at 4° C. by shaking for 10 minutes each time. Covered with fresh PBS buffer, the cells are visualized and photographed with confocal laser scanning microscopy (CLSM)

Figure 8:
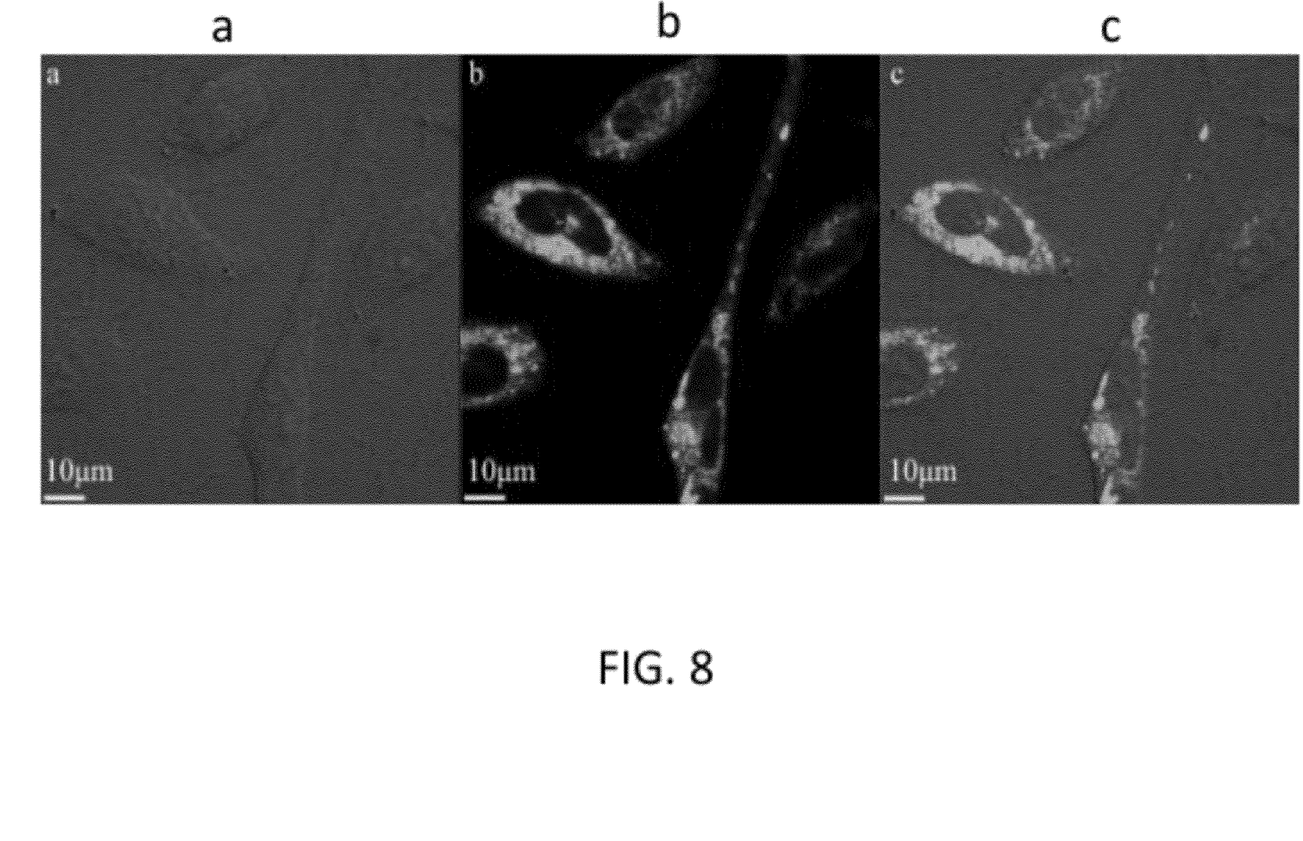

FIG. 8 shows the photos of the Au nanocluster treated 3T3 cells under a confocal laser scanning microscope. Photo (a) is a phase contrast image of the cells; photo (b) is a fluorescent image of cells; photo (c) is a merged image of photo (a) and (b). The Au nanocluster probes were specifically located to the mitochondria dispersed throughout the cell cytoplasm. The stained 3T3 mitochondria show a bright green emission.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Additional general background, which helps to show variations and implementations, may be found in the following publications, all of which are hereby incorporated by reference herein for all purposes: US Patent Application Publications US 2010/0009427 A1.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A fluorescent metal nanocluster bioprobe, comprising: a peptide templated fluorescent metal nanocluster, wherein said peptide molecule has a structure of X-Z chemical formula wherein X and Z are covalently bonded, X being a chemical side group selected from a chemical functional groups consisting of hydroxybenzene, carboxylic, guanidino, amide, sulfhydryl, amidocyanogen, indole and imidazole, Z being a specific peptide sequence for targeting a specific biological target, X being either at the N-terminal or the C-terminal of Z; said metal being either gold or silver and said metal atom and said peptide molecule form a nanocluster complex structure that emits fluorescent light under sufficient exciting condition, and wherein said peptide templated fluorescent metal nanocluster is produced by an one-step reaction of mixing a solution of said peptide molecule with a solution of either chloroauric acid or silver nitrate at a sufficient molar ratio under ambient temperature at sufficient pH for a sufficient period of time.

2. The fluorescent metal nanocluster bioprobe of claim 1, wherein X is a side group of an amino acid selected from a group consisting of amino acids of Arg, Asn, Asp, Cys, Gln, Glu, H is, Trp and Tyr.

3. The fluorescent metal nanocluster bioprobe of claim 1, wherein Z is a signal peptide sequence that targets an organelle of a cell selected from nucleus, nucleolus, endoplasmic reticulum, Golgi network, lysosome, mitochondrion, actin, microtubule, and cell membrane.

4. The fluorescent metal nanocluster bioprobe of claim 1, wherein Z is a specific binding sequence for a cellular biomolecule.

5. The fluorescent metal nanocluster bioprobe of claim 4, wherein Z is a ligand sequence for a molecule selected a group comprising of epidermal growth factor receptor, integrin, somatostatin receptor, gastrin-releasing peptide receptor, cholecystokinin-2/gastrin receptor, melanocortin-1 receptor and glucagon-like peptide-1 receptor.

6. The fluorescent metal nanocluster bioprobe of claim 1, wherein the metal nanocluster gives a narrow emission wavelength.

7. The fluorescent metal nanocluster bioprobe of claim 1, wherein said peptide and said metal salt is mixed at molar ratio ranging between 100:1 to 1:200.

8. A method of synthesizing a fluorescent metal nanocluster bioprobe, comprising actions of:

mixing a peptide solution with a solution of either chloroauric acid or silver nitrate at a sufficient molar ratio under ambient temperature at alkaline pH for a sufficient period of time, wherein said peptide includes a structure of X-Z chemical formula wherein X and Z are covalently bonded, X being a chemical functional group selected from chemical functional groups consisting of hydroxybenzene, carboxylic, guanidino, amide, sulfhydryl, amidocyanogen, indole and imidazole, Z being a specific peptide sequence for targeting a specific biological target, X being either at the N-terminal or the C-terminal side of Z, and said gold or silver metal atom and said peptide molecule form a nanocluster complex structure under ambient temperature and sufficient pH, wherein said structure emits fluorescent light under sufficient exciting condition.

9. The method of claim 8, wherein X is a side group of an amino acid selected from a group consisting of amino acids of Arg, Asn, Asp, Cys, Gln, Glu, His, Trp and Tyr.

10. The method of claim 8, wherein Z is a signal peptide sequence that targets an organelle of a cell selected from nucleus, nucleolus, endoplasmic reticulum, Golgi network, lysosome, mitochondrion, actin, microtubule, and cell membrane.

11. The method of claim 8, wherein Z is a specific binding sequence for a cellular biomolecule.

12. The method of claim 8, wherein Z is a ligand sequence for a molecule selected from epidermal growth factor receptor, integrin, somatostatin receptor, gastrin-releasing peptide receptor, cholecystokinin-2/gastrin receptor, melanocortin-1 receptor and glucagon-like peptide-1 receptor.

13. The method of claim 8, wherein the metal nanocluster generates a fluorescent emission of a narrow wavelength.

14. The method of claim 8, wherein said peptide and said metal salt are mixed at molar ratio ranging between 100:1 to 1:200.

15. A kit for generating a fluorescent metal nanocluster bioprobe, comprising:

a volume of alkaline solution;

a volume of a metal salt solution of either chloroauric acid or silver nitrate;

a control peptide solution; and a set of said metal salt solutions of different concentrations;

wherein said alkaline solution is used for adjusting pH of a reaction, said set of metal salt solutions is used to react with a user provided peptide solution for optimizing reaction molar ratio, and said control peptide is used for confirmation of a successful reaction condition, wherein said user-provided peptide has an X-Z structure chemical formula wherein X and Z are covalently bonded, X being a chemical functional group selected from a group of hydroxybenzene, carboxylic, guanidino, amide, sulfhydryl, amidocyanogen, indole and imidazole, Z being a specific peptide sequence for targeting a specific biological target, X being either at the N-terminal or the C-terminal side of Z and said metal atom being either gold or silver, and said user provided peptide is to be mixed with at least one of said set of metal solution to form a fluorescent nanocluster structured complex of said user provided peptide and said metal atom.

16. The kit of claim 15, wherein said X is an amino acid group selected from a group of amino acids of Arg, Asn, Asp, Cys, Gln, Glu, His, Trp and Tyr.

* * * * *

SEQUENCE LISTING

```
<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Synthesized

<400> SEQUENCE: 1

Cys Cys Tyr Thr Ala Thr
```

```
1               5
```

<210> SEQ ID NO 2
<211> LENGTH: 11
<212> TYPE: PRT
<213> ORGANISM: Artificial Sequence
<220> FEATURE:
<223> OTHER INFORMATION: Synthesized

<400> SEQUENCE: 2

```
Val Val Val Cys Cys Cys Arg Lys Val Val Cys
1               5                   10
```

<210> SEQ ID NO 3
<211> LENGTH: 7
<212> TYPE: PRT
<213> ORGANISM: Artificial Sequence
<220> FEATURE:
<223> OTHER INFORMATION: Synthesized

<400> SEQUENCE: 3

```
Cys Phe Phe Lys Asp Glu Leu
1               5
```

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

```
Gly Ala Ser Asp Tyr Gln Arg Leu Gly Cys
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

```
Cys Lys Gly Gly Ala Cys Leu
1               5
```

<210> SEQ ID NO 6
<211> LENGTH: 5
<212> TYPE: PRT
<213> ORGANISM: Artificial Sequence
<220> FEATURE:
<223> OTHER INFORMATION: Synthesized

<400> SEQUENCE: 6

```
Lys Phe Glu Arg Gln
1               5
```

<210> SEQ ID NO 7
<211> LENGTH: 25
<212> TYPE: PRT
<213> ORGANISM: Artificial Sequence
<220> FEATURE:
<223> OTHER INFORMATION: Synthesized

<400> SEQUENCE: 7

```
Leu Leu Tyr Arg Ser Ser Cys Leu Thr Arg Thr Ala Pro Lys Phe Phe
1               5                   10                  15
```

Arg Ile Ser Gln Arg Leu Ser Leu Met
            20                  25

<210> SEQ ID NO 8
<211> LENGTH: 7
<212> TYPE: PRT
<213> ORGANISM: Artificial Sequence
<220> FEATURE:
<223> OTHER INFORMATION: Synthesized

<400> SEQUENCE: 8

Ala Val Trp Ala Pro Met Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthesized

<400> SEQUENCE: 9

Asn Leu Arg Ile Ala Leu Arg
1               5

<210> SEQ ID NO 10
<211> LENGTH: 18
<212> TYPE: PRT
<213> ORGANISM: Artificial Sequence
<220> FEATURE:
<223> OTHER INFORMATION: Synthesized

<400> SEQUENCE: 10

Gly Trp Trp Leu Ala Leu Ala Leu Ala Ala Leu Ala Leu Ala Leu Trp
1               5                   10                  15

Trp Ala

<210> SEQ ID NO 11
<211> LENGTH: 7
<212> TYPE: PRT
<213> ORGANISM: Artificial Sequence
<220> FEATURE:
<223> OTHER INFORMATION: Synthesized

<400> SEQUENCE: 11

Arg Lys Cys Cys Tyr Ser Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthesized

<400> SEQUENCE: 12

Phe Cys Phe Trp Lys Thr Cys Thr
1               5

<210> SEQ ID NO 13
<211> LENGTH: 14
<212> TYPE: PRT
<213> ORGANISM: Artificial Sequence
<220> FEATURE:
<223> OTHER INFORMATION: Synthesized

<400> SEQUENCE: 13

Glu Gln Arg Leu Gly Asn Gln Trp Ala Val Gly His Leu Met
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Synthesized

<400> SEQUENCE: 14

Asp Tyr Met Gly Trp Met Asp Phe
1               5

<210> SEQ ID NO 15
<211> LENGTH: 13
<212> TYPE: PRT
<213> ORGANISM: Artificial Sequence
<220> FEATURE:
<223> OTHER INFORMATION: Synthesized

<400> SEQUENCE: 15

Ser Tyr Ser Met Glu His Phe Arg Trp Gly Lys Pro Val
1               5                   10

<210> SEQ ID NO 16
<211> LENGTH: 39
<212> TYPE: PRT
<213> ORGANISM: Artificial Sequence
<220> FEATURE:
<223> OTHER INFORMATION: Synthesized

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Cys Tyr Gly Ala Tyr Gly Trp Asp Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Synthesized

<400> SEQUENCE: 18

Arg Lys Cys Cys Tyr Ser Leu
1               5

<210> SEQ ID NO 19
<211> LENGTH: 11
<212> TYPE: PRT
<213> ORGANISM: Artificial Sequence
<220> FEATURE:

-continued

```
<223> OTHER INFORMATION: Synthesized

<400> SEQUENCE: 19

Tyr Gly Arg Lys Lys Arg Arg Gln Arg Arg Arg
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Synthesized

<400> SEQUENCE: 20

Tyr Arg Phe Lys
1
```